US009107567B2

(12) United States Patent
Pinho

(10) Patent No.: US 9,107,567 B2
(45) Date of Patent: Aug. 18, 2015

(54) SPECTRAL IMAGING WITH A COLOR WHEEL

(71) Applicant: CHRISTIE DIGITAL SYSTEMS USA, INC., Cypress, CA (US)

(72) Inventor: George P. Pinho, Waterloo, CA (US)

(73) Assignee: Christie Digital Systems USA, Inc., Cypress ( * ) Notice: Subject to any disclaimer, the term of this patent is extended or adjusted under 35 U.S.C. 154(b) by 223 days.

(21) Appl. No.: 13/728,736

(22) Filed: Dec. 27, 2012

(65) Prior Publication Data

US 2014/0187968 A1 Jul. 3, 2014

(51) Int. Cl.
*A61B 6/00* (2006.01)
*A61B 5/00* (2006.01)
*G01N 21/31* (2006.01)
*G01N 21/17* (2006.01)

(52) U.S. Cl.
CPC .......... *A61B 6/00* (2013.01); *A61B 5/0059* (2013.01); *A61B 5/441* (2013.01); *G01N 21/314* (2013.01); *G01N 2021/178* (2013.01); *G01N 2021/3144* (2013.01); *G01N 2021/3148* (2013.01)

(58) Field of Classification Search
None
See application file for complete search history.

(56) References Cited

U.S. PATENT DOCUMENTS

| | | |
|---|---|---|
| 6,503,195 B1 | 1/2003 | Keller et al. |
| 6,640,130 B1 | 10/2003 | Freeman et al. |
| 6,640,132 B1 | 10/2003 | Freeman et al. |
| 6,810,279 B2 | 10/2004 | Mansfield et al. |
| 6,937,885 B1 | 8/2005 | Lewis et al. |
| 6,958,809 B2 | 10/2005 | Sterling et al. |
| 6,989,891 B2 | 1/2006 | Braig et al. |
| 7,013,172 B2 | 3/2006 | Mansfield et al. |
| 7,050,157 B2 | 5/2006 | Braig et al. |
| 7,061,593 B2 | 6/2006 | Braig et al. |
| 7,239,909 B2 | 7/2007 | Zeman |
| 7,417,727 B2 | 8/2008 | Polonskiy et al. |
| 7,480,032 B2 | 1/2009 | Braig et al. |
| 7,713,294 B2 | 5/2010 | Bornstein |

(Continued)

FOREIGN PATENT DOCUMENTS

| | | | |
|---|---|---|---|
| CA | 2313923 A1 * | 1/2001 | ........... G03B 27/735 |
| EP | 1070985 A1 | 1/2001 | |
| WO | 2006102640 A2 | 9/2006 | |

OTHER PUBLICATIONS

Corresponding European Patent Application No. 13 198 190.4 Search Report dated Apr. 9, 2014.

*Primary Examiner* — Long V Le
*Assistant Examiner* — Kevin Pontius
(74) *Attorney, Agent, or Firm* — Perry + Currier Inc.

(57) ABSTRACT

A spectral imaging apparatus includes an image sensor positioned to capture images of a target, a rotating color wheel aligned with the image sensor, and a projector positioned to project overlay images onto the target. The color wheel can include one or more filter segments, each allowing light of a different range of wavelengths to pass. The color wheel can further include a blocking or opaque segment. A set of captured images of the different wavelengths can be processed to generate a false-color overlay image for projection onto the target. Processing of overlay images can be performed when the blocking or opaque segment is in front of the image sensor. The spectral imaging apparatus may be a multi-spectral imaging apparatus and made be used in the medical fields, such as for determining and indicating tissue oxygenation. Video rates can be achieved.

21 Claims, 6 Drawing Sheets

(56) References Cited

U.S. PATENT DOCUMENTS

| | | |
|---|---|---|
| 7,738,085 B2 | 6/2010 | Braig et al. |
| 7,850,305 B2 | 12/2010 | Hirihara et al. |
| 7,872,734 B2 | 1/2011 | Braig et al. |
| 7,884,933 B1 | 2/2011 | Kashyap et al. |
| 7,896,498 B2 | 3/2011 | Munger et al. |
| 8,224,425 B2 | 7/2012 | Freeman et al. |
| 8,509,879 B2 * | 8/2013 | Durkin et al. .............. 600/473 |
| 2002/0154300 A1 | 10/2002 | Mansfield et al. |
| 2002/0173723 A1 | 11/2002 | Lewis et al. |
| 2003/0086073 A1 | 5/2003 | Braig et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0139667 A1 | 7/2003 | Hewko et al. |
| 2004/0132167 A1 | 7/2004 | Rule et al. |
| 2004/0236229 A1 | 11/2004 | Freeman et al. |
| 2005/0007584 A1 | 1/2005 | Mansfield et al. |
| 2005/0049467 A1 | 3/2005 | Stamatas et al. |
| 2006/0247514 A1 | 11/2006 | Panasyuk et al. |
| 2006/0253261 A1 | 11/2006 | Maier et al. |
| 2006/0268258 A1 | 11/2006 | Braig |
| 2006/0281068 A1 | 12/2006 | Maier et al. |
| 2007/0002276 A1 | 1/2007 | Hirohara et al. |
| 2007/0016079 A1 | 1/2007 | Freeman et al. |
| 2007/0024946 A1 | 2/2007 | Panasyuk et al. |
| 2007/0038042 A1 | 2/2007 | Freeman et al. |
| 2007/0158569 A1 | 7/2007 | Zeman |
| 2007/0178067 A1 | 8/2007 | Maier et al. |
| 2007/0232930 A1 | 10/2007 | Freeman et al. |
| 2007/0249913 A1 | 10/2007 | Freeman et al. |
| 2007/0268485 A1 | 11/2007 | Polonskiy et al. |
| 2008/0007692 A1 | 1/2008 | Mihashi et al. |
| 2008/0183059 A1 | 7/2008 | LaPlante et al. |
| 2009/0053816 A1 | 2/2009 | Tezel et al. |
| 2009/0118622 A1 | 5/2009 | Durkin et al. |
| 2009/0137908 A1 | 5/2009 | Patwardhan |
| 2009/0149726 A1 | 6/2009 | Hyde et al. |
| 2009/0213360 A1 | 8/2009 | Braig et al. |
| 2009/0225277 A1 | 9/2009 | Gil |
| 2009/0275841 A1 | 11/2009 | Melendez et al. |
| 2010/0056928 A1 | 3/2010 | Zuzak et al. |
| 2010/0113940 A1 | 5/2010 | Sen et al. |
| 2010/0160791 A1 | 6/2010 | Liu et al. |
| 2010/0185064 A1 | 7/2010 | Bandic et al. |
| 2010/0185067 A1 | 7/2010 | Gupta |
| 2010/0203024 A1 | 8/2010 | Terman et al. |
| 2010/0210931 A1 | 8/2010 | Cuccia et al. |
| 2010/0249547 A1 | 9/2010 | Braig et al. |
| 2010/0267842 A1 | 10/2010 | Kiral et al. |
| 2010/0284917 A1 | 11/2010 | Kustner et al. |
| 2011/0111449 A1 | 5/2011 | Braig et al. |

* cited by examiner

SPECTRAL IMAGING WITH A COLOR WHEEL

FIELD

This disclosure relates to imaging, and more particularly, to spectral imaging.

BACKGROUND

Multi-spectral and hyper-spectral imagers are 2D imaging devices that collect spectral information over a spectral range, such as discrete wavelength ranges (multi-spectral) or continuous wavelength ranges (hyper-spectral). Such devices may be used to obtain spatially resolved spectral information for applications such as agriculture and food processing where spectrally and spatially resolved information can be used to assess moisture in crops and bruising in fruits. Similar technology is also used in medical applications to determine tissue oxygen level, for example.

The typical device uses a 2D imager and optics containing a dispersing prism or grating. The device operates as a line scanner in which a sample passing by the device is scanned and the incoming light is dispersed onto an imager. As the device completes the scan of the object, an image of the object is created that is spectrally resolved. The spectrally resolved image can then be devolved into individual wavelengths allowing for identification of chemicals that contribute to the spectral response in the image. As an example, identifying a water spectral component in such an image enables users to then encode the image for water content and show the chemical signature of water in the image. This is one application of spectral imaging for crop fields. Another type of spectral imager captures a full field image for each wavelength. In this type of design, the object is illuminated at various wavelengths and for each wavelength, an image is captured. The captured image cube can then be analyzed and chemically resolved to display the chemical of interest in a multi-wavelength image. Another alternative to the above design uses a tunable filter or a set of optical filters that are scanned past the imager to generate the image cube for chemical encoding.

One drawback of the above techniques is processing speed, which is governed by either how fast the object can move past the spectral line scanner or how quickly each wavelength can be captured in the imager. For applications where it is not possible for the object to be moving, such as a patient, the acquisition time can be very long. A chemically encoded image may take tens of seconds to generate, making it infeasible for real-time measurements.

SUMMARY

A rotating color wheel filters light from a target captured by an image sensor. Captured images can be processed into overlay images that can be projected back onto the target. In addition to one or more filter segments, the color wheel can include a blocking or opaque segment and processing of overlay images can be performed when the blocking or opaque segment prevents capture of target light at the image sensor. The color wheel can be rotated and the image processing and projection can be performed at video rates.

BRIEF DESCRIPTION OF THE DRAWINGS

The drawings illustrate, by way of example only, embodiments of the present invention.

DETAILED DESCRIPTION

It is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

It should also be understood that the functions, processes, and methods described in this specification may be embodied in programs stored in memory and executable by a processor. Programs may indeed be implemented in software for execution by various types of processors. An identified program of executable code may, for instance, comprise one or more physical or logical blocks of computer instructions, which may, for instance, be organized as an object, procedure, class, function, or similar programmatic entity. Nevertheless, the executables of an identified program need not be physically located together, but may comprise disparate instructions stored in different locations which, when joined logically together, comprise the program and achieve the stated purpose for the program.

A program may also be implemented as a hardware circuit comprising custom VLSI circuits or gate arrays, off-the-shelf semiconductors such as logic chips, transistors, or other discrete components. A program may also be implemented in programmable hardware devices such as field programmable gate arrays, programmable array logic, programmable logic devices or the like.

Indeed, a program of executable code may be a single instruction, or many instructions, and may even be distributed over several different code segments, among different programs, and across several memory devices. Similarly, operational data may be identified and illustrated herein within programs, and may be embodied in any suitable form and organized within any suitable type of data structure. The operational data may be collected as a single data set, or may be distributed over different locations including over different storage devices, and may exist, at least partially, merely as electronic signals on a system or network. The programs may be passive or active, including agents operable to perform desired functions.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

Figure 1:
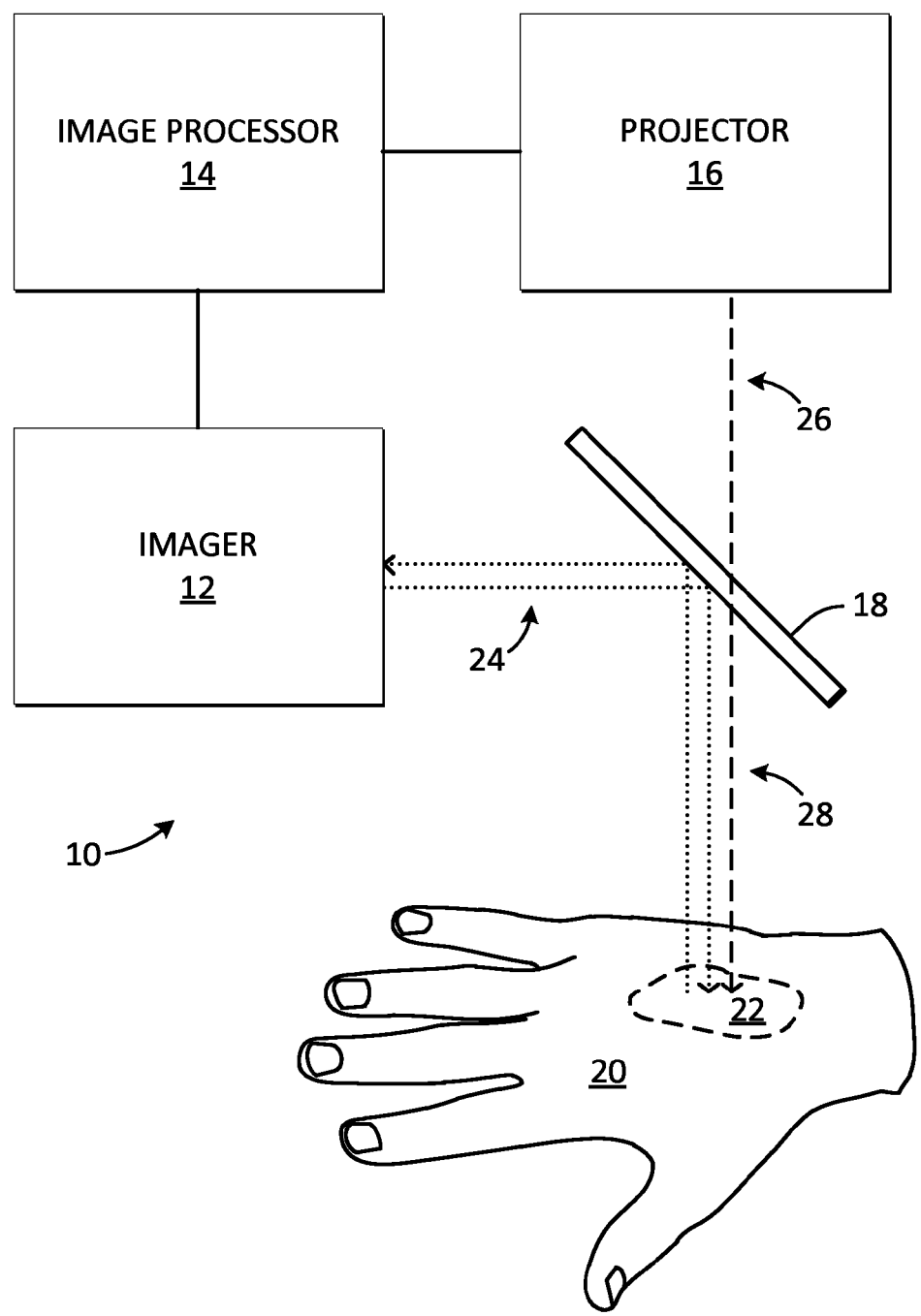
FIG. 1 is a block diagram of a spectral imaging apparatus according to embodiments of the present invention.

FIG. 1 illustrates a spectral imaging apparatus 10 according to an embodiment of the present invention. The spectral imaging apparatus 10 may be known as a multi-spectral imaging apparatus or a hyper-spectral imaging apparatus. The spectral imaging apparatus 10 will be described in the context of medical use, however, it should be understood that the apparatus 10 may find use in other fields, such as food processing or agriculture.

The imaging apparatus 10 includes an imager 12, an image processor 14, a projector 16, and an optical filter 18. The image processor 14 is connected to the imager 12 and the projector 16, and is configured to process image information collected by the imager 12 and output image information to the projector 16. The imager 12 and projector 16 collect light from and emit light onto a target object, such as a target tissue 20 (e.g., a region of a patient's skin surface) via the filter 18. As will be discussed, the imaging apparatus 10 is capable of spectral tissue oxygenation measurements, measuring and processing spectral information at video-rate speeds, and projecting a chemically encoded oxygen map directly back onto the target tissue.

Tissue oxygen level plays a key role in managing patient wounds and in surgical procedures where tissue viability is important. In specific applications such as burn wounds, amputations, diabetic ulcers, and cosmetic surgery, tissue oxygen level can be a direct measure of tissue health and healing progress. The imaging apparatus 10 can assist physicians and other healthcare workers in assessing tissue health in real-time or near real-time, that is, at video rates, in order to augment or possibly replace experience and direct visual inspection. As a result, patients can experience shorter healing cycles due to reduced chance of infection or repeating of procedures. This may also reduce the burden on the healthcare system.

The imager 12 emits light onto a region 22 of the target tissue 20 to illuminate the region 22 of target tissue 20. The region 22 is a portion of target tissue that is of interest and can include, for example, a portion of a patient's skin or another organ or portion thereof.

The filter 18 is configured to allow some light to pass while reflecting remaining light. The filter 18 may include a bandpass filter, a shortpass filter, a notch filter, a dichroic filter, or the like. The filter 18 is arranged to reflect the illumination light emitted by the imager 12 onto the target tissue 20 and to direct light reflected from the target tissue 20 along an imaging optical path 24 back to the imager 12. The imaging optical path 24 extends between the target tissue 20 and the imager 12. In this embodiment, the band pass filter 18 is tilted at about 45 degrees with respect to the imaging optical path 24 at the imager 12.

The imager 12 captures light reflected from the target tissue 20 along the imaging optical path 24 via the band pass filter 18.

In this embodiment, illumination light emitted from the imager 12 also travels along the imaging optical path 24. However, it should be understood that light emitted by the imager 12 need not be entirely coincident with light reflected to the imager 12 from the target tissue 20 in order for both emitted light and incoming light to be considered to share the imaging optical path 24. In other embodiments, illumination light is emitted along a different optical path.

The image processor 14 is configured to generate overlay images (frames), such as false color images, referencing light captured by the imager 12. The image processor 14 provides the overlay images to the projector 16.

The projector 16 is arranged to project overlay images along a projecting optical path 26 and onto the target tissue 20. The projector 16 can be any suitable kind of projector 16 and may include an I/O interface for connecting to the image processor 14, a controller for controlling operations of the projector 16, a projection light source (lamp, laser, LED), and an imaging device, such as LCD light valves, a digital micromirror device (DMD), or similar.

The projecting optical path 26 extends from the projector 16 to the target tissue 20 via the filter 18. The projecting optical path 26 at least partially overlaps the imaging optical path 24, as shown at 28. In this embodiment, the optical paths 24, 26 overlap between the filter 18 and the target tissue 20, and do not overlap between the filter 18 and the imager 12 or projector 16. The projecting optical path 26 and the imaging optical path 24 partially overlapping (coaxial alignment) in this manner is advantageous in that overlay images can be projected directly onto the object (e.g., tissue 20) being examined and will remain aligned irrespective of focus distance or projection angle.

The filter 18 is arranged along the projecting optical path 26 and the imaging optical path 24, and specifically where these paths intersect, so as to reflect specific wavelengths of light while allowing other wavelengths to pass. In this embodiment, the imager 12 emits light of a set of wavelengths. (A set or subset of wavelengths can include a range of wavelengths or a discrete one or more wavelengths.) The filter 18 is selected to reflect at least a subset of the set of wavelengths towards the target tissue 20, with light of the remaining wavelengths passing through the filter 18 and out of the system. Light of the subset of wavelengths strikes the target tissue 20 and a further subset of wavelengths is reflected from the target tissue 20 back towards the filter 18, which reflects most or all of the further subset of light to the imager 12. This further subset of wavelengths of light is representative of a characteristic of the target tissue 20 being measured, such as tissue oxygenation, and is processed by the image processor 14 into at least one overlay image that is projected by the projector 16. The overlay image can be generated with reference to the properties of the filter 18, so that most or all of the light of the overlay image projected by the projector 16 passes through the filter 18 and onto the target tissue 20. Irrespective of the wavelength composition of the overlay image, the filter 18 reflects away light emitted by the projector 16 that would be erroneously captured by the imager 12. Naturally, the color composition of the overlay images can be selected so that all information of interest is projected onto the target tissue 20. However, it is advantageous that the filter 18 ensures that very little, if any, light emitted by the projector 16 enters the system at the imager 12, since such light may introduce error.

Figure 2:
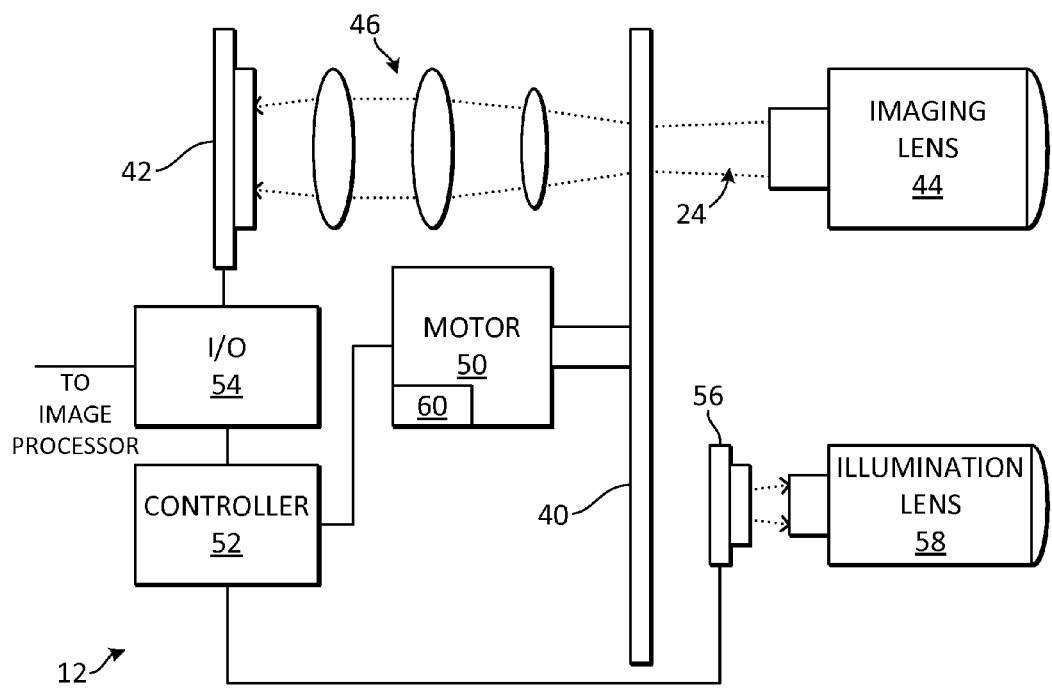
FIG. 2 is a block diagram of the imager.

Referring to FIG. 2, which shows components of an embodiment of the imager 12, a color wheel 40 is used in the capture of light of the further subset of wavelengths that is reflected from target tissue 20.

The imager 12 includes the color wheel 40 positioned between an image sensor 42 and an imaging lens 44, which is positioned to capture light reflected from the target tissue 20. In this embodiment, the imager 12 further includes a series of relay lenses 46 (illustrated schematically) positioned between the color wheel 40 and the image sensor 42. In another embodiment, such as that shown in FIG. 10, the color wheel 40 is located in front of the image sensor 42 and the relay lenses 46 are located behind the imaging lens 44. That is, the relay lenses 46 are located between the color wheel 40 and the imaging lens 44. The color wheel 40 may be placed where the diameter of the light rays is smallest as this advantageously allows the color wheel 40 to be made as small as possible. To achieve this, the relay lenses 46 can be selected and arranged to provide an image beam that is compressed.

The image sensor 42 can be selected as a high-speed and high-sensitivity CMOS sensor, such as those commercially available from ON Semiconductor of Phoenix, Ariz. Examples of such sensors include those available under product numbers LUPA300 and LUPA1300. These are merely illustrative examples, and other image sensors having suitable frame rates and sensitivities can be used.

The lenses 44, 46 can be selected for the particular geometry and optical characteristics desired.

The color wheel 40 is aligned with the image sensor 42 on the imaging optical path 24. The color wheel 40 is configured to rotate at a predetermined frequency, such as at least about 15 Hz to attain minimally acceptable video frame rates. The color wheel 40 includes at least one filter segment and at least one light blocking (e.g., opaque) segment, as will be discussed below.

The imager 12 further includes, in this embodiment, a motor 50 connected to the color wheel 40 to rotate the color wheel 40, a controller 52 connected to the motor 50, an input/output (I/O) circuit 54 connected to the controller 52 and to the image sensor 42, and an illumination device that includes a illumination source 56 and an illumination lens 58 arranged to illuminate the target tissue 20. The imager 12 can further include a housing (not shown) to contain its components.

The motor 50 has a shaft that connects to the center of the color wheel 40 to rotate the color wheel 40. The motor 50 can be any suitable kind of motor.

The controller 52 includes a processor or similar device configured to control operation of the motor 50. The controller 52 can reference output of the image sensor 42 to determine which segment of the color wheel 40 is currently aligned with the imaging optical path 24 and to maintain a predetermined constant speed of rotation for the color wheel 40. That is, when output of the image sensor 42 is above a threshold amount (e.g., threshold intensity), then the controller 52 determines that a filter segment is currently in front of the image sensor 42. Conversely, when output of the image sensor 42 is below the threshold amount, then the controller 52 determines that the blocking segment is currently in front of the image sensor 42. Such determinations can be made periodically to measure and control the rotational frequency of the color wheel 40. As such, the image sensor can be considered to also be a rotational position sensor for the color wheel 40.

In other embodiments, the motor 50 can include a rotational position sensor 60 that provides rotational position measurements of the motor 50 and thus the color wheel 40 to the controller 52. The controller 52 can be configured to reference signals received from the rotational position sensor 60 to maintain a predetermined constant speed of rotation for the color wheel 40. The rotational position sensor 60 can also be referenced by the controller 52 to determine which segment of the color wheel 40 is currently aligned with the imaging optical path 24.

The controller 52 is further configured to control illumination of the illumination source 56, which can include a whilelight LED, combination of wavelength matched LEDs, a Xenon (Xe) lamp or wavelength matched lasers to emit light onto the target tissue 20. The controller 52 can synchronize light emissions from the light source with reference to the rotational position of the color wheel 40. In this embodiment, the controller 52 turns off the light source whenever a blocking segment of the color wheel 40 blocks light on the imaging optical path 24, which can advantageously save power. This also has the benefit of projecting images onto a non-illuminated or lesser-illuminated surface so as to improve image quality.

The controller 52 is further configured to control the I/O circuit 54 to capture images whenever a filter segment of the color wheel 40 is aligned with the imaging optical path 24. In some embodiments, the controller 52 and I/O circuit 54 are parts of the same integrated circuit.

The I/O circuit 54 outputs images captured by the image sensor 42 to the image processor 14. The I/O circuit 54 can be any suitable kind of input/output interface.

Figure 3:
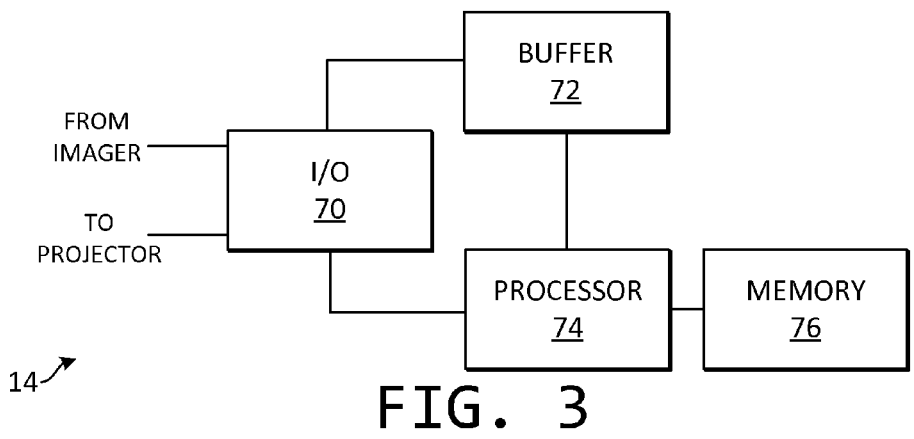
FIG. 3 is a block diagram of the image processor.

FIG. 3 illustrates an embodiment of the image processor 14. The image processor 14 includes an I/O circuit 70, a buffer 72 connected to the I/O circuit 70, a processor 74 connected to the I/O circuit 70 and the buffer 72, and memory 76 connected to the processor 74.

The I/O circuit 70 receives captured images from the imager 12 (specifically, the I/O circuit 54) and outputs overlay images to the projector 16. The I/O circuit 70 can be any suitable kind of input/output interface. In some embodiments, the I/O circuit 70 can be merged with the I/O circuit 54 of the imager 12, particularly when the imager 12 and the image processor 14 are provided together in the same housing.

The buffer 72 receives captured images from the I/O circuit 70 and buffers the captured images for the processor 74. In some embodiments, output from the image sensor 42 is only buffered when the rotational position sensor (e.g., the image sensor 42, a separate sensor 60, etc) indicates that the image sensor 42 is capturing suitable images. The buffer 72 can be any suitable kind of buffer memory and may include a data buffer, a framebuffer, or similar.

The processor 74 is configured by, for example, a program to process captured images in the buffer 72 into overlay images, as will be discussed in detail below. The processor 74 can be further configured to provide overlay images to the projector 16 for projection whenever a blocking segment of the color wheel 40 blocks the imaging optical path 24 by, for example, referencing the rotational position of the color wheel 40. The processor 74 can be any suitable kind of processor 74 capable of processing images of the selected resolution in the amount of time defined by the frequency of rotation of the color wheel 40.

The memory 76 can include any combination of short-term and long-term storage such as RAM, ROM, cache memory, flash memory, a hard-drive, and the like. The memory 76 stores programs that are executed by the processor 74 and can further provide working storage space for processing of images.

Operation of the medical imaging apparatus 10 will now be discussed in more detail with reference to FIGS. 4 and 5, which respectively illustrate an embodiment of the color wheel 40 and a related timing diagram.

The color wheel 40 includes at least one filter segment 80-88 and at least one light blocking (e.g., opaque) segment 90. In the example illustrated, five filter segments 80-88 are provided and a single blocking segment 90 is provided. The filter segments are the same size and together span 180 degrees of the color wheel 40, with the blocking segment spanning the remaining contiguous 180 degrees.

The filter segments 80-88 are configured to allow light of different wavelengths to pass and to block light of other wavelengths. The filter segments 80-88 can include narrow bandpass filters chosen to match absorption bands of oxygenated hemoglobin. In this example, each of the filter segments 80-88 has a different center wavelength. Two or more absorption bands can be used to compute the concentration of oxygenated hemoglobin. Generally, more absorption bands (filter segments) provide increased accuracy.

The blocking segment 90 is configured to block light from the image sensor 42 (FIG. 2) at times when the projector 16 (FIG. 1) is projecting. The blocking segment 90 can include black, opaque material.

The relative sizes of the filter segments 80-88 and blocking segment 90 can be selected to determine the amount of time available for image capture and image processing/projecting. In this example, the blocking segment 90 is selected to occupy 50% of the color wheel 40, thereby allowing the filter segments 80-88 to occupy the remaining 50% of the color wheel 40. Since the color wheel 40 rotates at a constant frequency, the image capture time and image processing/projecting time are approximately equal. The filter segments 80-88 can all have the same size, as in the illustrated example, or can have different sizes thereby allowing different times for capture of different wavelengths.

The absorption spectra for oxygenated and deoxygenated hemoglobin tend to be in the visible and near-infrared spectrums. The color wheel filter segments and filter 18 (FIG. 1) can be selected and configured accordingly.

In some embodiments, the filter 18 is a shortpass filter selected to transmit wavelengths of about 450 nm to about 650 nm and reflect wavelengths of greater than about 650 nm, up to about 850 nm. Accordingly, visible light leaves the system while near-infrared light is reflected between the imager 12 and target 20. The color wheel filter segments can have center wavelengths selected within the 650 to 850 nm range according to known wavelengths of response for oxygenated and deoxygenated hemoglobin, so as to enhance differences in oxygenated and deoxygenated hemoglobin. Alternatively, the color wheel filter segments can be selected to have center wavelengths that are evenly spaced within the 650 to 850 nm range. The projector 16 can thus use the visible light spectrum of about 450 nm to about 650 nm to project clear and crisp images. In these embodiments, use of near-infrared light for imaging allows for penetration into the tissue 20 to provide for a bulk assessment of tissue oxygenation.

In other embodiments, the filter 18 is a notch filter selected to reflect wavelengths between about 500 to 600 nm and allow other wavelengths of light to pass and leave the system. Accordingly, this range of visible light is reflected between the imager 12 and target 20. The color wheel filter segments can have center wavelengths selected within the 500 to 600 nm range according to known wavelengths of response for oxygenated and deoxygenated hemoglobin, so as to enhance differences in oxygenated and deoxygenated hemoglobin. Alternatively, the color wheel filter segments can be selected to have center wavelengths that are evenly spaced within the 500 to 600 nm range. The projector 16 uses visible light wavelengths outside the 500 to 600 nm range for projection. In these embodiments, use of visible light for imaging allows for a surface assessment of tissue oxygenation, as visible light does not substantially penetrate tissue.

The spectral imaging apparatus 10 can be made modular, so as to readily provide for bulk and/or surface tissue analysis. The color wheel 40 and filter 18 can be configured as modules, so that they can be selected and installed at the time of manufacture. The color wheel 40 and filter 18 can further be removable and replaceable, so that the apparatus 10 can be reconfigured after being put into service. The image processor 14 can be configured to support both bulk and surface tissue analysis, or can be configured to be updatable to support bulk or surface tissue analysis depending on the selection of the color wheel 40 and filter 18.

Figure 4:
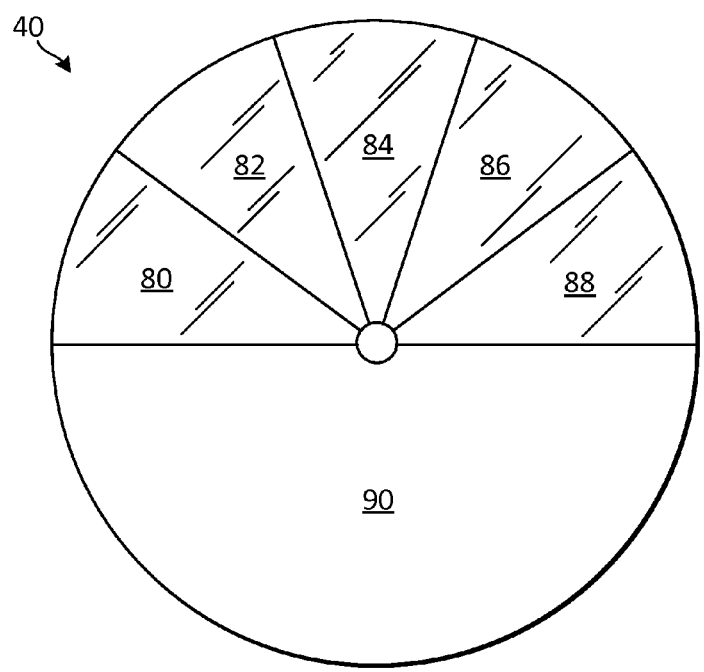
FIG. 4 is a front view of the color wheel.
Figure 5:
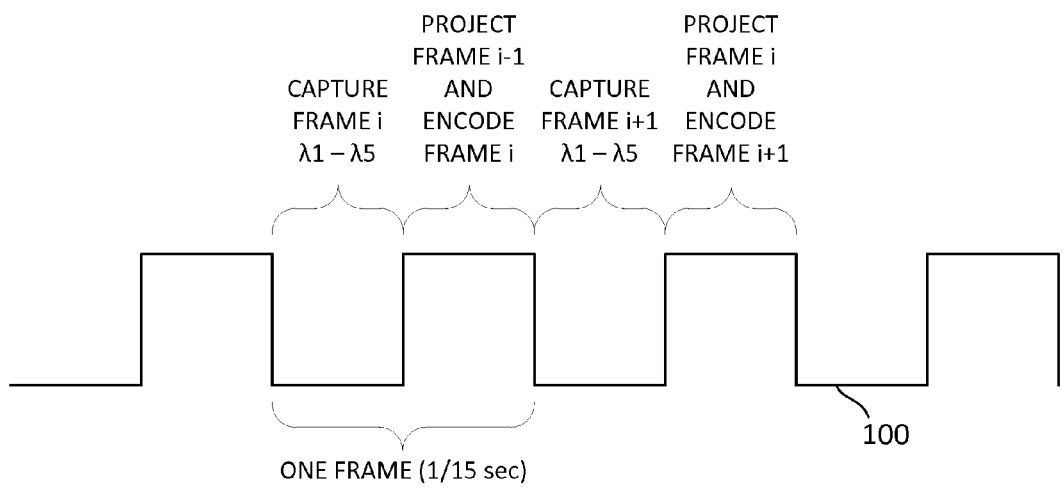
FIG. 5 is a timing diagram of the spectral imaging apparatus.

FIG. 5 illustrates the different times during which capture and processing/projecting is performed for the example color wheel 40 of FIG. 4. Half of the period for one frame, that is, half of 1/15 seconds (i.e., 0.033 s), is dedicated to capturing images of the five wavelengths defined by the filter segments 80-88. During the other half of the period, when the blocking segment 90 blocks the capture of light, a spectral overlay image (frame) to encode for oxygen is processed and a previously processed overlay image is displayed. Because suitable processing time is required to encode oxygen concentration information into overlay images, captured images are buffered and projected overlay images lag by at least one frame, so that each displayed overlay image is at least one frame behind the current image being processed. In this example, since separate images for the five wavelengths are captured within 0.033 seconds, the image sensor 42 (FIG. 2) is selected to have an acquisition speed of 150 frames per second. The waveform 100 illustrated represents, in some embodiments, the output of the rotational position sensor 60 or the comparison of the output of the image sensor 42 with the threshold output amount, where positive and negative edge triggering indicates to the processor 74 (FIG. 3) what is to be performed at a given time.

As the speed of rotation of the color wheel 40 is increased, sets of images of the different wavelengths provided by the filter segments 80-88 are captured and processed into overlay images, such that overlay images form frames of a real-time video that is projected onto the object (e.g., tissue 20) at video rates, such as 15 or more frames per second.

Figure 6:
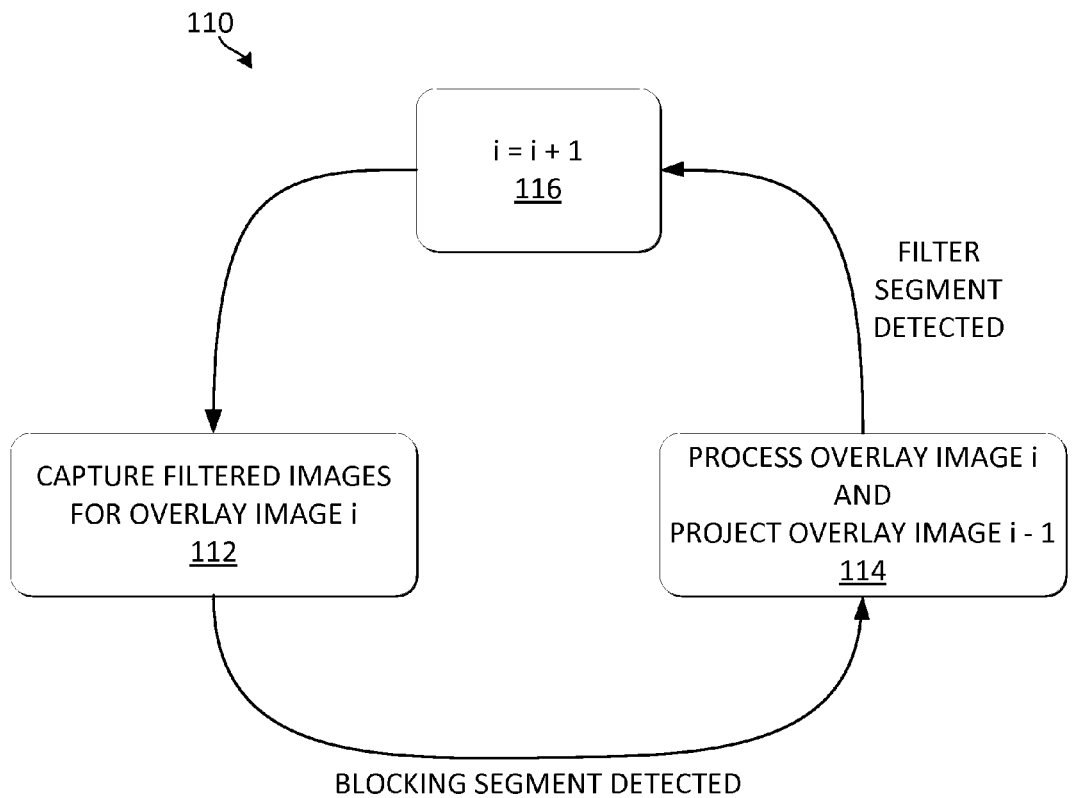
FIG. 6 is a state diagram illustrating a method of timing the capture, processing, and projecting of images according to embodiments of the present invention.

FIG. 6 illustrates a state diagram for a method 110 of timing the capture, processing, and projecting of images according to an embodiment of the present invention. The method 110 can be used with the spectral medical imaging apparatus 10, and specifically, can be programmed to be performed by the processor 74 (FIG. 3) of the image processor 14.

Figure 7:
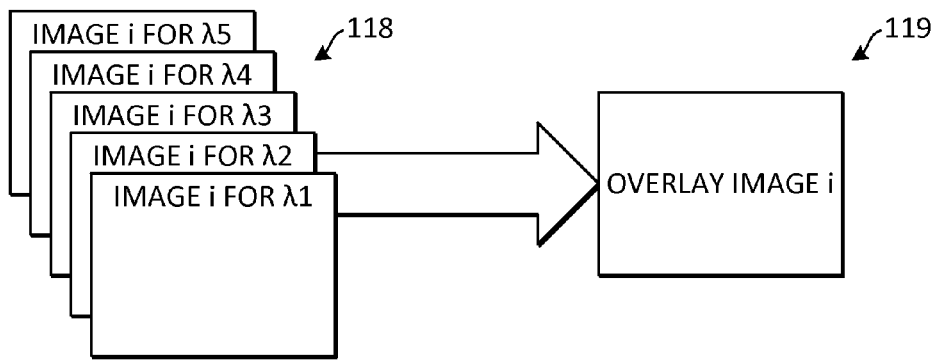
FIG. 7 is a schematic diagram of a set of captured images and a generated overlay image.

At 112, images are captured by the image sensor 42 when the orientation of the color wheel 40 causes light provided to the image sensor 42 to be filtered. As several filter segments 80-88 are used, a set of multiple captured images 118 of different wavelength bands are captured during the same cycle, i, of the color wheel 40 for use in generating one overlay image 119, as shown in FIG. 7.

At 114, when the blocking segment 90 blocks light from being captured by the image sensor 40, the multiple images of different wavelength bands that were captured during the same cycle, i, of the color wheel 40 are processed to generate an overlay image. At least partially contemporaneously with such processing of captured images, a previously generated overlay image of a previous cycle, i−1, is projected onto the target tissue. While the projected image lags by one frame, it is advantageous that the video-rate nature of overlay image projection makes this lag imperceptible.

When a filter segment is next detected, the cycle index, i, is advanced, at 116. The cycle index, i, can be used to store images in the memory 76 (FIG. 3) and may be used by the processor 74 to identify a particular overlay image or set of captured images.

The filter segments of the color wheel 40 can be selected so that each of the spectrally resolved captured images represents an image showing an absorption pattern of both oxygenated and deoxygenated hemoglobin at a particular wavelength. To compute the relative concentrations of each, a reference spectrally resolved image which takes into account sensor response, illumination profile on the tissue, and any background lighting can be obtained. The reference image is measured using the apparatus 10 on a sample of Spectralon, which is a standard material available from LabSphere with nearly 100% lambertian distribution and 99.9% reflectivity. In addition, to the reference image, the dark level intensity at the image sensor 42 (FIG. 2) can also be measured to remove any dark noise resident on the CMOS device and elsewhere in the system. The reference image and the dark level image can be measured prior to each measurement taken of the tissue 20 (FIG. 1) or other object. Alternatively, a reference image and dark level image can be factory set and stored in memory 76 (FIG. 3) for later computation.

To compute the oxygen concentration, the processor 74 (FIG. 3) can ratio the measured absorption intensity, reference spectra, and dark level intensity to compute a reflectance ratio, R(λ) for each of the captured images at the respective wavelength, λ:

$$R(\lambda) = \frac{I_o - I_b}{I_m - I_b}$$

Here $I_o$ is the reference image, $I_b$ is the dark level image, and $I_m$ is the measured patient image all at wavelength, λ.

The reflectance ratio can be related to the absorption coefficient by the Beer-Lambert equation and can be expressed as a linear combination of the contribution of oxygenated and deoxygenated hemoglobin to the measured absorption.

$$\ln(R(\lambda_i)) = (\epsilon_{HbO2}(\lambda_i)C_{HbO2} + \epsilon_{Hb}(\lambda_i)C_{Hb})L$$

where, ε is the molar extinction coefficient for the combination of oxygenated and deoxygenated hemoglobin at each wavelength, C is the concentration of oxygenated and deoxygenated hemoglobin, and L is a constant representing an absorption path length. In the example color wheel 40 having five filter segments 80-88, the above equation results in a linear set of five equations, one for each measured wavelength. The equations are solved by a least squares fit of the oxygenated and deoxygenated hemoglobin concentrations. The processor 74 can perform this pixel by pixel. The percent oxygenation is then calculated from:

$$S_{O2} = \frac{C_{HbO2}}{C_{HbO2} + C_{Hb}} \times 100$$

and a resulting overlay image is generated by the processor 74 with each pixel representing a percent oxygen level in the image. Each pixel can then be color encoded to visually represent the oxygen concentration over the entire overlay image. Suitable colors for the overlay image can be selected based on the target (e.g., patient's skin) and ambient lighting conditions (e.g., hospital indoor lighting).

The above calculations can be stored in the memory 76 of the image processor 14 (FIG. 3) as instructions executable by the processor 74.

Figure 8:
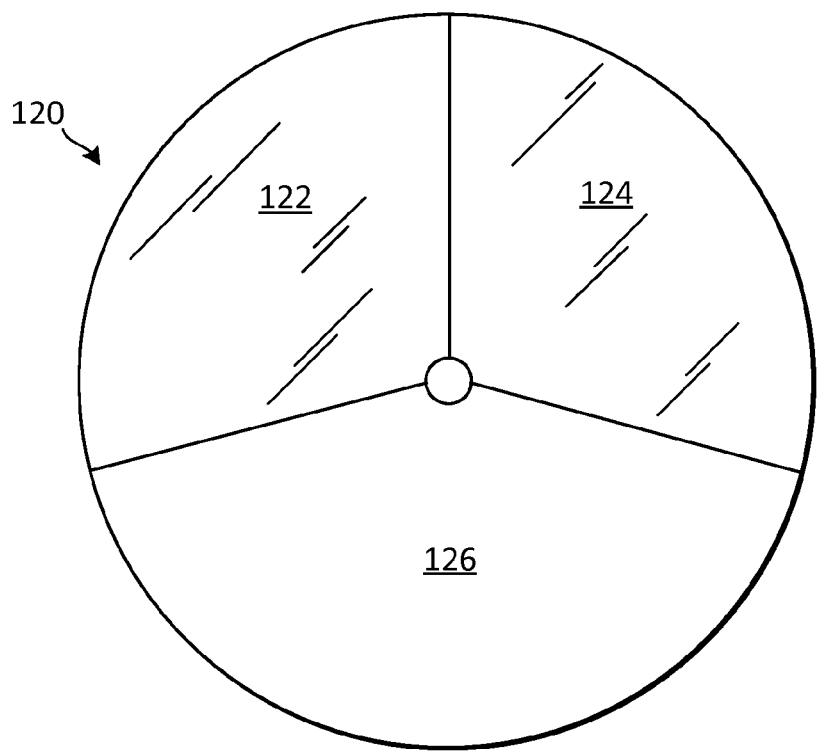
FIG. 8 is a front view of a color wheel according to another embodiment of the present invention.

FIG. 8 shows a color wheel 120 according to another embodiment. The color wheel 120 can be used with any of the apparatuses and methods described herein. The color wheel 120 includes two filter segments 122, 124 selected for different wavelengths and one blocking segment 126. The blocking segment 126 occupies less than 180 degrees of the color wheel 120. In another embodiment, the blocking segment 126 occupies more than 180 degrees of the color wheel 120.

Figure 9:
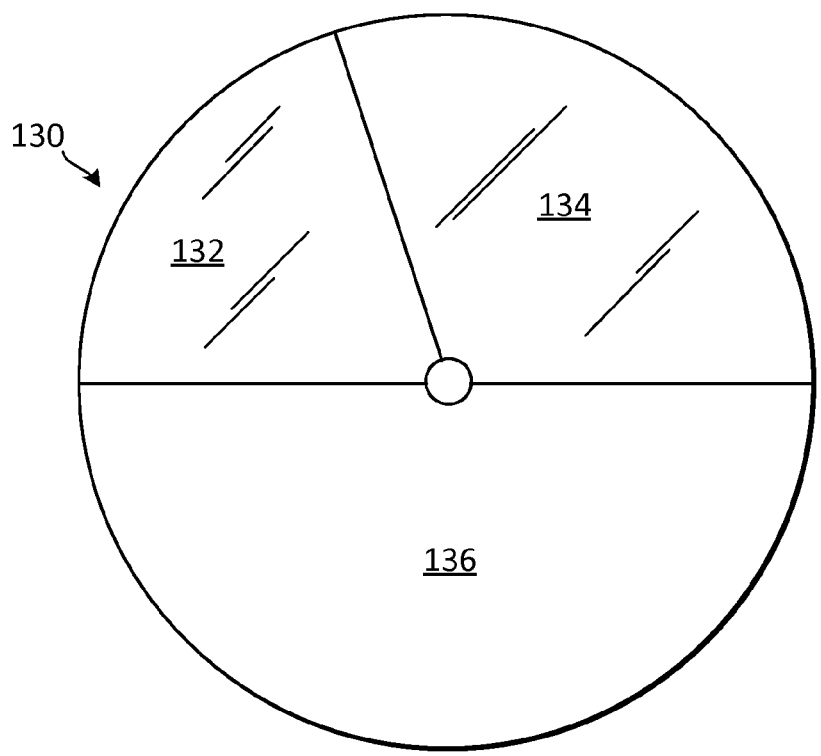
FIG. 9 is a front view of a color wheel according to yet another embodiment of the present invention.

FIG. 9 shows a color wheel 130 according to another embodiment. The color wheel 130 can be used with any of the apparatuses and methods described herein. The color wheel 130 includes two filter segments 132, 134 selected for different wavelengths and one blocking segment 134. In this embodiment, the filter segments 132, 134 are not the same size. In other embodiments, other quantities of different-sized filter segments are provided. When the color wheel rotates at a constant speed, filter segments of larger sizes increase the time for light collection and can thus be useful for improving collection efficiency at wavelengths where the available signal is low. After capture and during processing (e.g., at 114 of FIG. 6), signal correction can be performed to scale the signal back down to normalize signal intensity ratios. This may improve the signal-to-noise ratio at wavelengths where the signal is weak. For wavelengths where the signal is expected to be relatively stronger, filter segments can be made smaller.

Figure 10:
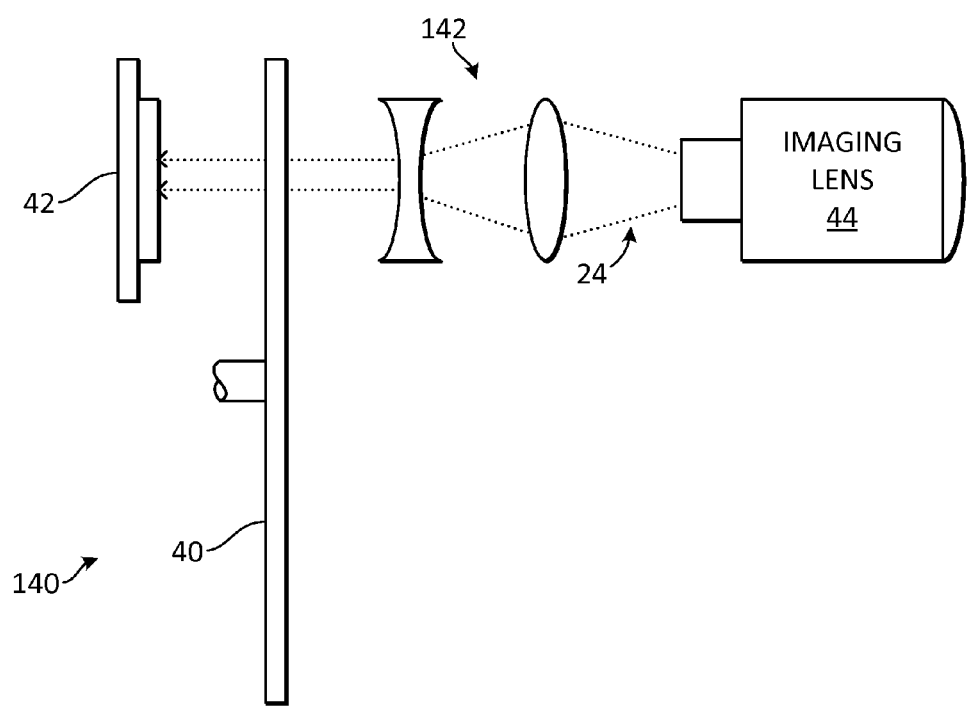
FIG. 10 is a block diagram of a portion of an imager according to another embodiment.

FIG. 10 shows a portion of an imager 140 according to another embodiment. The imager 140 is similar to the imager 12 of FIG. 2 and only differences will be discussed in detail. The imager 140 can be used with any of the apparatuses and methods described herein. The imager 140 includes one or more relay lenses 142 (illustrated schematically) located between the imaging lens 44 and the color wheel 40, which is located directly in front of the image sensor 42. As shown, the relay lenses are configured to reduce the beam width at the color wheel 40 so as to reduce the size of the color wheel 40. In still other embodiments, one or more relay lenses are located between the image sensor 42 and the color wheel 40 and one or more relay lenses are located between the color wheel 40 and the imaging lens 44.

As can be understood from the above, the apparatus and methods provided by the present invention advantageously allow for real-time video projection of false-color overlay images onto the target being examined. Although the main example is described with respect to tissue oxygenation in the medical arts, the present invention may find use in other fields where real-time overlay images are needed.

While the foregoing provides certain non-limiting example embodiments, it should be understood that combinations, subsets, and variations of the foregoing are contemplated. The monopoly sought is defined by the claims.

What is claimed is:

1. A spectral video medical imaging apparatus comprising:
an illumination device arranged to illuminate a target tissue;
an image sensor arranged to capture light reflected from the target tissue along an imaging optical path;
a color wheel aligned with the image sensor on the imaging optical path, the color wheel configured to rotate at a predetermined frequency, the color wheel comprising at least one filter segment and at least one blocking segment;
a projector arranged to project overlay images along a projecting optical path and onto the target tissue, the projecting optical path at least partially overlapping the imaging optical path; and
a processor connected to the image sensor and the projector, the processor configured to generate the overlay images from light captured by the image sensor and to provide the overlay images to the projector for projection when the blocking segment blocks the imaging optical path;
wherein
the projection occurs intermittently and at different times than the capturing; and
the blocking segment is configured to block the light reflected from the target tissue along the imaging optical path from reaching the image sensor when the projector is projecting the overlay images.

2. The apparatus of claim 1, wherein the processor is further configured to, during a current cycle of the color wheel, encode a first image based on light captured by the image sensor during the current cycle and control the projector to project a first image encoded during a previous cycle of the color wheel that occurred earlier than the current cycle.

3. The apparatus of claim 1, wherein the filter segment is selected to match an absorption band of oxygenated hemoglobin.

4. The apparatus of claim 1, wherein the color wheel comprises two or more filter segments.

5. The apparatus of claim 4, wherein the filter segments are selected to have different wavelengths to match different absorption bands of oxygenated hemoglobin.

6. The apparatus of claim 1, wherein the color wheel comprises a single blocking segment.

7. The apparatus of claim 1, further comprising a filter arranged along the projecting optical path and the imaging optical path, the filter configured to reflect wavelengths of light that the filter segment of the color wheel transmits.

8. The apparatus of claim 7, wherein the filter is located at an intersection of the projecting optical path and the imaging optical path and the filter is oriented at about 45 degrees to both the projecting optical path and the imaging optical path.

9. The apparatus of claim 8, wherein the projecting optical path overlaps the imaging optical path between the filter and the target tissue.

10. The apparatus of claim 9, wherein the projecting optical path does not overlap the imaging optical path between the filter and the image sensor.

11. The apparatus of claim 1, further comprising an imaging lens, the color wheel being positioned between the image sensor and the imaging lens.

12. The apparatus of claim 11, further comprising at least one relay lens positioned between the color wheel and the image sensor.

13. The apparatus of claim 11, further comprising at least one relay lens positioned between the color wheel and the imaging lens.

14. The apparatus of claim 1, wherein the predetermined frequency of rotation of the color wheel is at least about 15 Hz.

15. A method of video imaging, the method comprising:
    capturing images of a target tissue, the images being of different wavelength bands defined by a color wheel comprising at least one filter segment and at least one blocking segment;
    processing captured images to generate overlay images;
    projecting the overlay images onto the target tissue when the blocking segment blocks capturing images of the target tissue; and
    timing the capturing, processing, and projecting according to the rotation of the color wheel to perform the projecting of a previously generated overlay image at least partially contemporaneously with the processing of current captured images;
    wherein the projecting occurs intermittently and at different times than the capturing.

16. The method of claim 15, wherein the different wavelength bands are selected to match different absorption bands of oxygenated hemoglobin.

17. The method of claim 15, wherein the color wheel comprises a single blocking segment.

18. The method of claim 15, wherein the capturing and projecting are performed at least partially along a same optical path.

19. The method of claim 15, comprising rotating the color wheel at least about 15 Hz.

20. A spectral video imaging apparatus comprising:
    a processor;
    memory connected to the processor;
    an image sensor connected to the processor, the image sensor positioned to capture images of a target;
    a projector connected to the processor, the projector positioned to project overlay images onto the target; and
    a color wheel aligned with the image sensor, the color wheel including a blocking segment and at least two filter segments of different wavelengths, the color wheel configured to rotate at a predetermined frequency;
    the processor configured to process a set of images of the different wavelengths captured by the image sensor to generate a false-color overlay image, and provide the overlay image to the projector for projection onto the target;
    wherein the projection occurs intermittently and at different times than the capturing; and the blocking segment is configured to block the image capture when the projector is projecting the overlay images.

21. The apparatus of claim 20, wherein the processor is configured to process a set of images of the different wavelengths to generate a false-color overlay image and provide the overlay image to the projector according to predetermined video-rate frequency of rotation of the color wheel.

* * * * *